United States Patent
Kouge

(10) Patent No.: US 11,446,060 B2
(45) Date of Patent: Sep. 20, 2022

(54) SENSOR INSERTION DEVICE

(71) Applicant: PHC Holdings Corporation, Tokyo (JP)

(72) Inventor: Masahiro Kouge, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 196 days.

(21) Appl. No.: 16/963,121

(22) PCT Filed: Jan. 28, 2019

(86) PCT No.: PCT/JP2019/002651
§ 371 (c)(1),
(2) Date: Jul. 17, 2020

(87) PCT Pub. No.: WO2019/176331
PCT Pub. Date: Sep. 19, 2019

(65) Prior Publication Data
US 2021/0045774 A1   Feb. 18, 2021

(30) Foreign Application Priority Data
Mar. 16, 2018   (JP) .............................. JP2018-049702

(51) Int. Cl.
*A61B 17/34*   (2006.01)
*A61B 5/145*   (2006.01)

(52) U.S. Cl.
CPC ...... *A61B 17/3468* (2013.01); *A61B 5/14503* (2013.01); *A61B 5/14532* (2013.01); *A61B 2017/3492* (2013.01)

(58) Field of Classification Search
CPC ............ A61B 17/3468; A61B 5/14503; A61B 5/14532; A61B 2017/3492
See application file for complete search history.

(56) References Cited

U.S. PATENT DOCUMENTS 9,247,900 B2 *  2/2016  Brister .............. A61B 5/14865
9,662,071 B2    5/2017  Ohkoshi
(Continued)

FOREIGN PATENT DOCUMENTS

JP    2005160789 A  *  6/2005
JP    2008-506468        3/2008
(Continued)

OTHER PUBLICATIONS

International Search Report dated Apr. 16, 2019 in International (PCT) Application No. PCT/JP2019/002651.

*Primary Examiner* — Alex M Valvis
*Assistant Examiner* — Grace L Rozanski
(74) *Attorney, Agent, or Firm* — Wenderoth, Lind & Ponack, L.L.P.

(57) ABSTRACT

A sensor insertion device includes a cylindrical main body case that has a lower end opening and an upper end opening; a needle insertion button that is disposed slidably in and out of the upper end opening of the cylindrical main body case; a carrier that is provided inside the cylindrical main body case and linked to the needle insertion button; a guide needle holder that is provided at a lower end portion of the carrier and configured to detachably hold a guide needle for guiding a sensor in an insertion direction; a cylindrical needle extraction sleeve that is provided slidably around an outer periphery of the cylindrical main body case; and a grip portion that is provided along a lengthwise direction of the cylindrical main body case on an outer periphery of the cylindrical needle extraction sleeve.

10 Claims, 15 Drawing Sheets

(56) References Cited

U.S. PATENT DOCUMENTS

| | | | |
|---|---|---|---|
| 10,499,853 B2 | 12/2019 | Ohkoshi | |
| 2003/0023189 A1* | 1/2003 | Kuo | A61B 10/0045 |
| | | | 600/584 |
| 2014/0187876 A1* | 7/2014 | Ohkoshi | A61B 5/72 |
| 2017/0078583 A1* | 3/2017 | Haggerty | A61B 1/00096 |
| 2017/0245798 A1 | 8/2017 | Ohkoshi | |
| 2019/0133638 A1* | 5/2019 | Ii | A61B 17/34 |

FOREIGN PATENT DOCUMENTS

| | | |
|---|---|---|
| JP | WO2013/035455 | 3/2013 |
| JP | WO2017/187943 | 11/2017 |
| WO | 2005/051183 | 6/2005 |
| WO | 2006/017358 | 2/2006 |

* cited by examiner

SENSOR INSERTION DEVICE

TECHNICAL FIELD

The present application relates to a sensor insertion device that inserts a sensor for measuring biological information into a patient's body in order to perform continuous blood glucose measurement, for example.

BACKGROUND ART

The configuration of a conventional sensor insertion device is as follows.

A conventional device comprises cylindrical elongated main body case having a lower end opening and an upper end opening, a needle insertion button provided slidably in and out of the upper end opening of the main body case, a carrier that is provided inside the main body case and is linked to the needle insertion button, a guide needle holder that is provided to the lower end portion of the carrier and holds a guide needle for guiding a sensor in the insertion direction, and a needle extraction sleeve that is provided slidably around the outer periphery of the main body case.

When this sensor insertion device is used to leave a sensor in the arm of a patient, the patient performs the needle insertion operation and the needle extraction operation with the sensor insertion device.

In the needle insertion operation, the patient brings the lower end of the sensor insertion device into contact with his arm. Then, when the patient presses the needle insertion button on the upper end, the carrier slides downward. At the lower end of the carrier, the guide needle and the sensor of the biological information measuring device guided by the guide needle are inserted into the patient's arm.

Next, in the needle extraction operation, when the patient pulls up on the needle extraction sleeve, the carrier slides upward, and the guide needle is pulled out of the patient's arm.

Consequently, the sensor of the biological information measuring device is left in the arm, and the attachment of the biological information measuring device is completed (see, for example, Japanese Unexamined Patent Application Publication No. 2008-506468).

SUMMARY

Technical Problem

A problem encountered with the conventional example given above is that the sensor insertion device was not easy to use.

Specifically, with a conventional sensor insertion device, in the needle insertion operation, the lower end of the slender sensor insertion device is brought into contact with the patient's arm, and the needle insertion button on the upper end is pressed with the thumb.

When the needle insertion button on the upper end is thus operated in a state in which the lower end of the slender sensor insertion device is in contact with the arm, pressing the button can change the alignment of the sensor insertion device, resulting in instability. As a result, the alignment of the sensor insertion device is unstable when the needle insertion button is operated, making the device more difficult to use.

In view of this, it is an object of the present invention to improve the usability of a sensor insertion device during a needle insertion operation.

Solution to Problem

To achieve this object, the sensor insertion device of the present invention is a sensor insertion device for inserting a sensor for measuring biological information into a patient's body, comprising a cylindrical main body case having a lower end opening and an upper end opening; a needle insertion button that is disposed slidably in and out of the upper end opening on the inside of the main body case, and that is operated by the user when performing needle insertion; a carrier that is provided in the main body case and is linked to the needle insertion button; a guide needle holder that is provided at the lower end portion of the carrier and that detachably holds a guide needle that is inserted into the body when guiding the sensor in the insertion direction; a long cylindrical needle extraction sleeve that is provided slidably around the outer periphery of the main body case; and a grip portion that is provided along the lengthwise direction of the main body case on the outer peripheral surface side of the needle extraction sleeve, and that is gripped by the user's hand when inserting the sensor.

This configuration achieves the intended purpose.

Advantageous Effects

Specifically, in the present invention, the needle extraction sleeve is formed in a long cylindrical shape, and its outer peripheral surface is provided with a grip portion along the lengthwise direction of the main body case.

Accordingly, in the needle insertion operation, when the patient presses the needle insertion button with the thumb, the patient can grasp the grip portion of the needle extraction sleeve with the four fingers (excluding the thumb) and the palm. This squeezing of the grip portion stabilizes the alignment of the sensor insertion device.

At this point, since the grip portion is provided along the lengthwise direction of the main body case, the axis formed by the squeezing hand and the pressing axis of the needle insertion button can be made to coincide.

Therefore, since the needle insertion button is pressed down along the axis formed by the squeezing hand in a state in which the alignment of the sensor insertion device is to stabilized, the sensor insertion device is less likely to shake.

As a result, the alignment of the sensor insertion device is stable, and the sensor insertion device is easier to use in the needle insertion operation.

DESCRIPTION OF EMBODIMENTS

An embodiment of the present invention will be described in detail below with reference to the drawings.

In the following embodiment, "upper" and "lower" mean "upper" and "lower" in the usage state (state of being attached to an upper arm 2) of the sensor insertion device 1 (an example of a sensor insertion device) shown in FIGS. 6A to 6C, etc.

Embodiment 1

Figure 1:
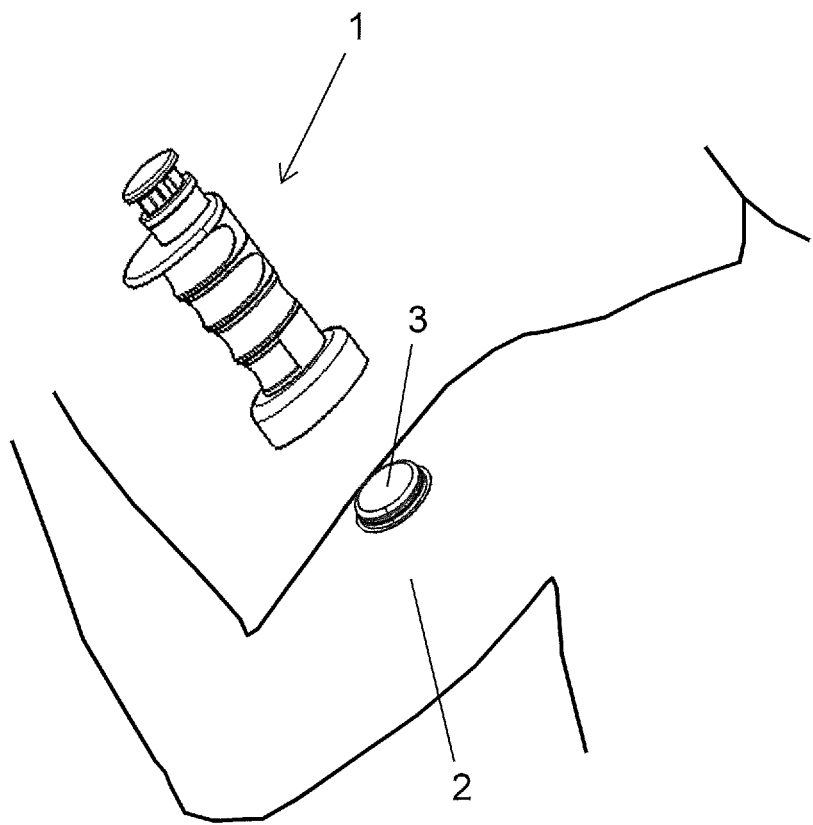
FIG. 1 is an oblique view of the sensor insertion device according to Embodiment 1 of the present invention, and of a biological information measuring device attached by using the sensor insertion device.

FIG. 1 shows the sensor insertion device 1 (an example of a sensor insertion device) and a biological information measuring device 3 attached to the upper arm 2 of a patient by means of the sensor insertion device 1. The biological information measuring device 3 measures blood glucose continuously; for example, it measures the blood glucose level every 5 minutes for 1 to 2 weeks in a row. This allows the user to ascertain the tendency of the to blood glucose state of the patient over a predetermined period, and the blood glucose state while asleep.

Figure 2:
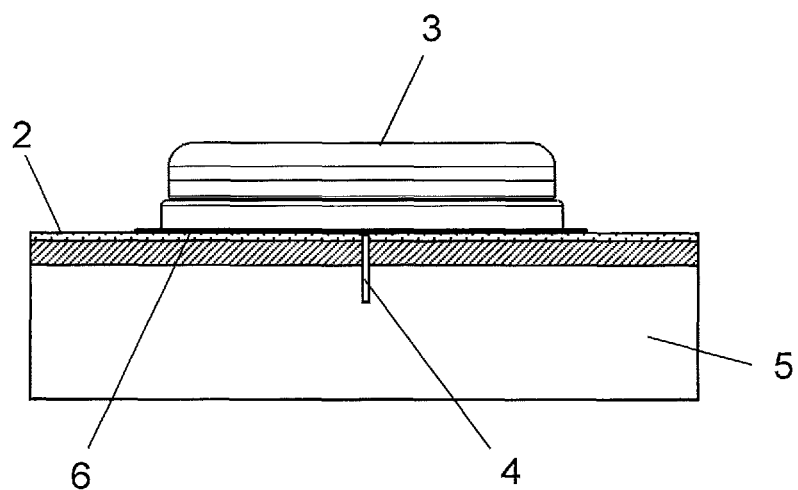
FIG. 2 is a view showing the attached state of the biological information measuring device in FIG. 1.

FIG. 2 is a diagram showing the attached state of the biological information measuring device 3 in FIG. 1.

A needle-shaped sensor 4 projects from the lower surface of the biological information measuring device 3. The sensor 4 is left in the upper arm 2 with its tip extending to the subcutaneous tissue 5. The sensor 4 is used to measure biological information, and measures the concentration of glucose (blood glucose level) in interstitial fluid, for example. The sensor 4 is inserted into the patient's body (such as into the upper arm 2) by the sensor insertion device 1.

Figure 3B:
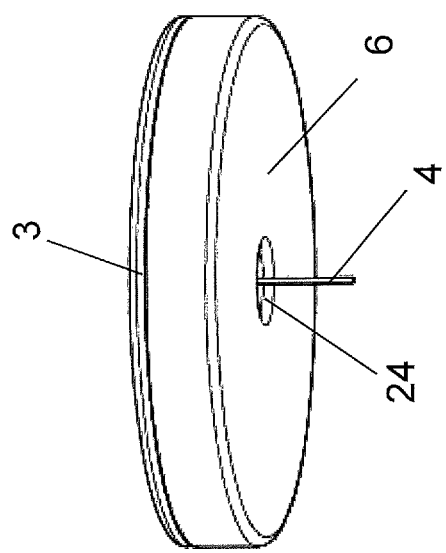
FIG. 3B is an oblique view of the biological information measuring device in FIG. 1 from below.
Figure 3A:
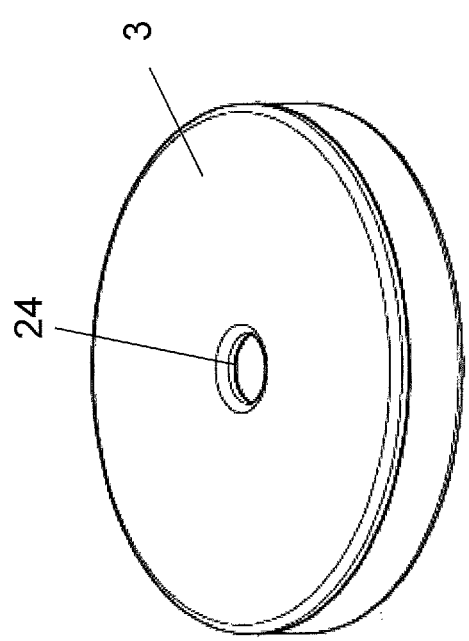
FIG. 3A is an oblique view of the biological information measuring device in FIG. 1 from above.

FIG. 3A is an oblique view of the biological information measuring device 3 as seen from above. The biological information measuring device 3 is formed in a disc shape. The lower part of the biological information measuring device 3 is provided with an adhesive portion 6, as shown in FIG. 3B, so that it will stick well to the patient's skin.

Figure 4:
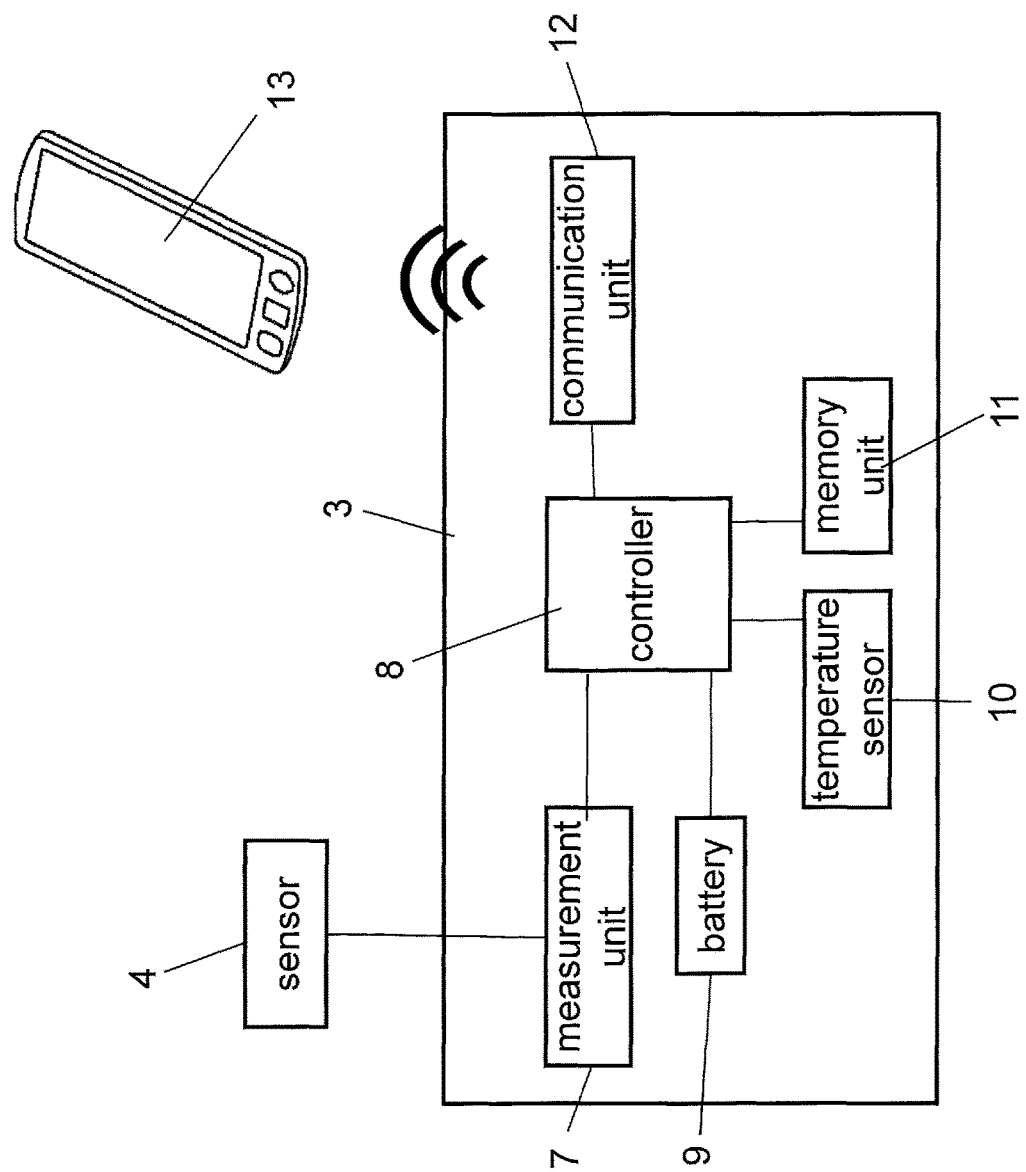
FIG. 4 is a control block diagram of the biological information measuring device in FIG. 1.

FIG. 4 is a control block diagram of the biological information measuring device 3.

The sensor 4 is connected to a measurement unit 7. The measurement unit 7 is connected to a controller 8. A battery 9, a temperature sensor 10, a memory unit 11, and a communication unit 12 are electrically connected to the controller 8.

With the biological information measuring device 3 in this embodiment, the measurement unit 7 uses the sensor 4 to measure the blood glucose level at regular time intervals (such as every 5 minutes). The controller 8 corrects the blood glucose level on the basis of the temperature sensed by the temperature sensor 10, and then stores it in the memory unit 11. The controller 8 also transmits measurement values to an external device (such as a mobile phone 13) via the communication unit 12.

Figure 5:
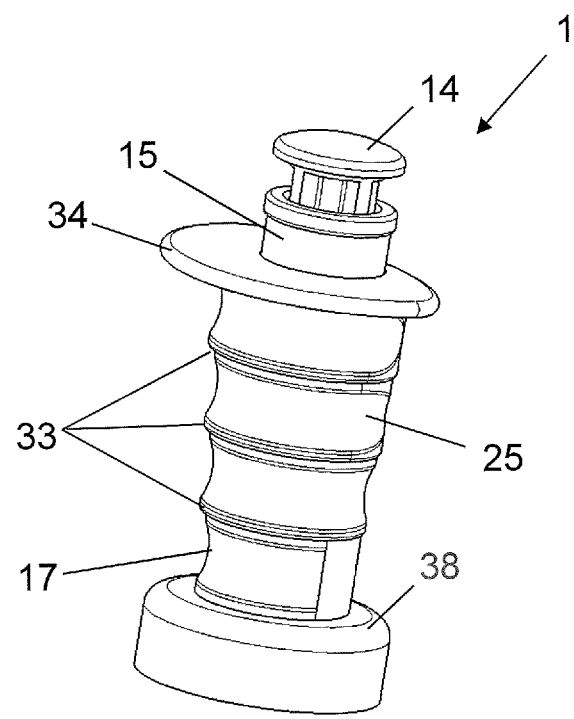
FIG. 5 is an oblique view of the sensor insertion device in FIG. 1.

The biological information measuring device 3 is attached to the upper arm 2 by using the sensor insertion device 1 shown in FIG. 5. More specifically, when the patient or other such user grasps the sensor insertion device 1 as shown in FIG. 6A and presses the needle insertion button 14 with his thumb as shown in FIG. 6B, the biological information measuring device 3 is attached to the upper arm 2.

The user of the sensor insertion device 1 may be the patient himself, or another party such as a nurse.

Also, as will be described in detail below, when the user uses the sensor insertion device 1 to attach the biological information measuring device 3 to the upper arm 2, the user performs inputs to the sensor insertion device 1 for needle insertion and needle extraction. In response to these inputs, the sensor insertion device 1 performs a needle insertion operation and a needle extraction operation.

The sensor insertion device 1 will now be described in further detail.

Figure 6A:
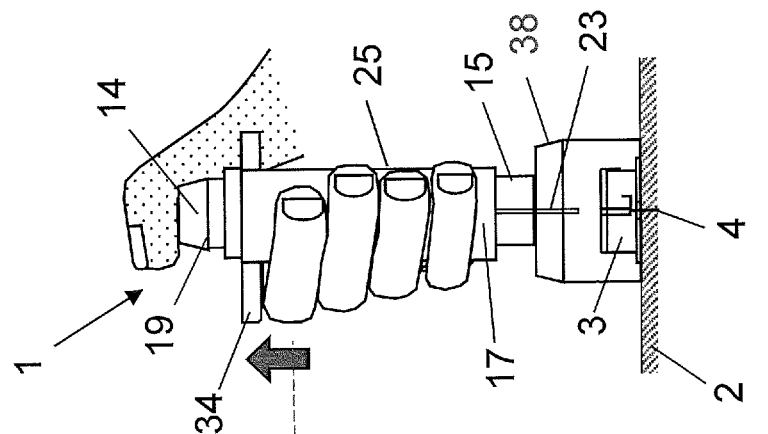
FIGS. 6A, 6B, and 6C are views showing the usage state of the sensor insertion device in FIG. 1.
Figure 6B:
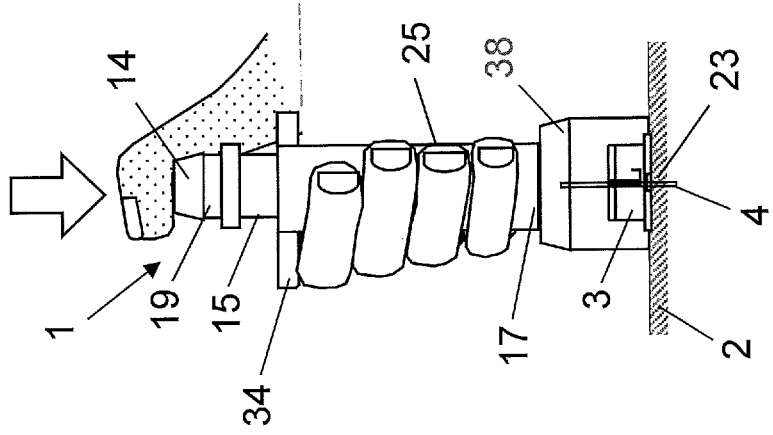
Figure 7:
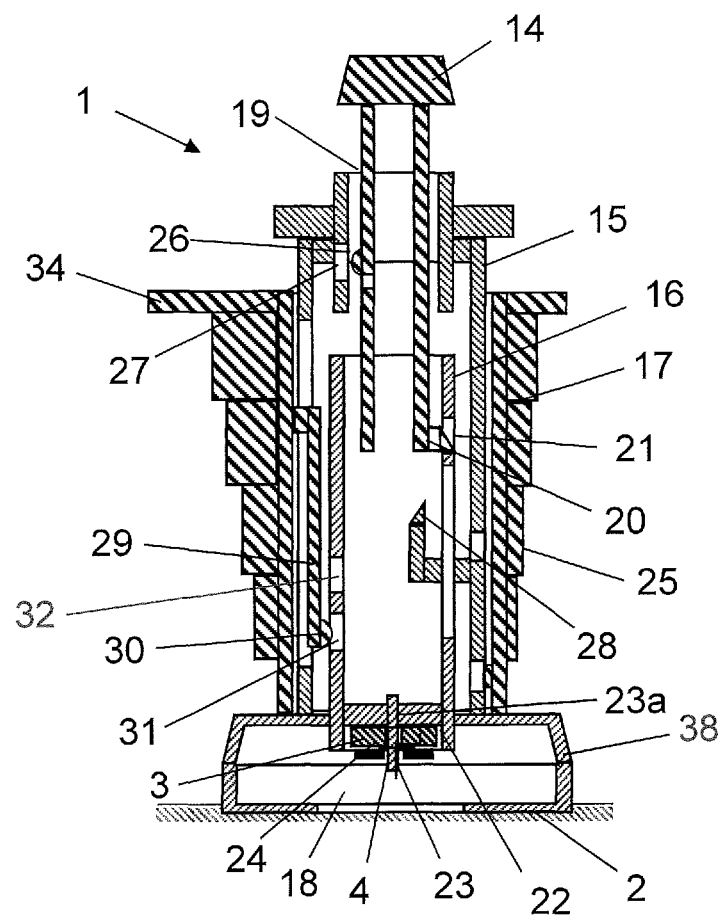
FIG. 7 is a cross section of the sensor insertion device in FIG. 6A.
Figure 8:
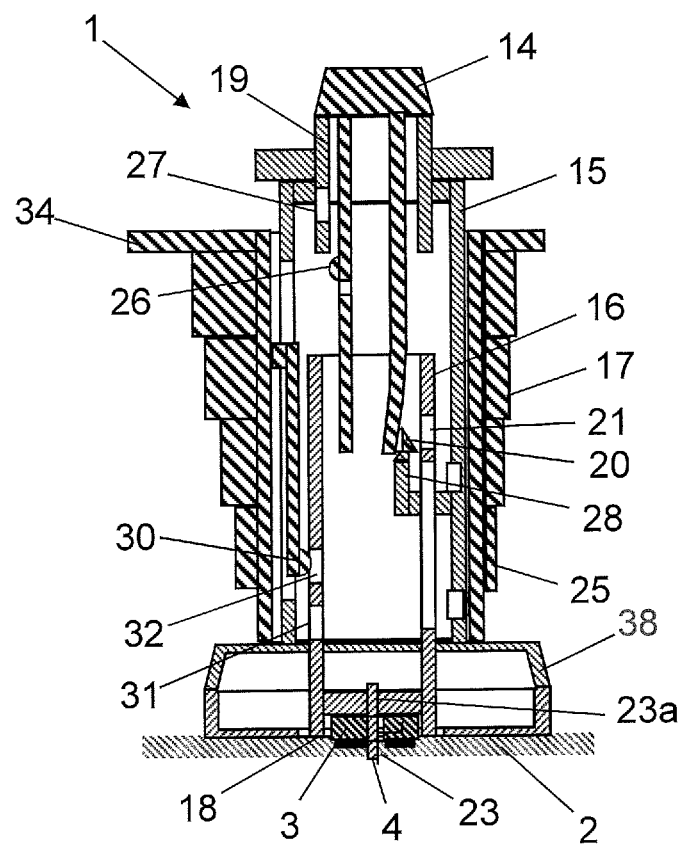
FIG. 8 is a cross section of the sensor insertion device in FIG. 6B.

FIG. 7 is a cross section of the sensor insertion device 1 in the state of FIG. 6A, and FIG. 8 is a cross section of the sensor insertion device 1 in the state of FIG. 6B.

As shown in FIGS. 5 and 7, the sensor insertion device 1 has a long cylindrical main body case 15, a needle insertion button 14 that is attached to the upper end side on the inner peripheral surface side of the main body case 15, a long cylindrical carrier 16 that is linked to the lower end of the needle insertion button 14, and a long cylindrical needle extraction sleeve 17 that is attached slidably around the outer periphery of the main body case 15.

The main body case 15 is molded from plastic. A lower end opening 18 is provided at the lower end of the main body case 15, and an upper end opening 19 is provided at the upper end.

The needle insertion button 14 has a manipulation portion that is pressed down by the user's thumb during the needle insertion operation, and a long cylindrical portion, and is molded from plastic. The needle insertion button 14 is provided slidably in and out of the upper end opening 19 of the main body case 15.

Also, the needle insertion button 14 has a pressing tab 20 that is provided at the lower end of the long cylindrical shape so as to project outward in the engagement direction, and engages with a pressing hole 21 formed so as to go through the wall surface of the carrier 16. This engagement links the carrier 16 and the needle insertion button 14.

The carrier 16 is molded from plastic in a long cylindrical shape. The carrier 16 is disposed slidably on the inner peripheral surface side of the main body case 15. A holder 22 of the biological information measuring device 3 is provided at the lower end of the carrier 16 (the lower part of FIG. 7).

The biological information measuring device 3 is detachably held by the holder 22. A guide needle holder 23a having a metal guide needle 23 is provided at the center of the holder 22.

Figure 9:
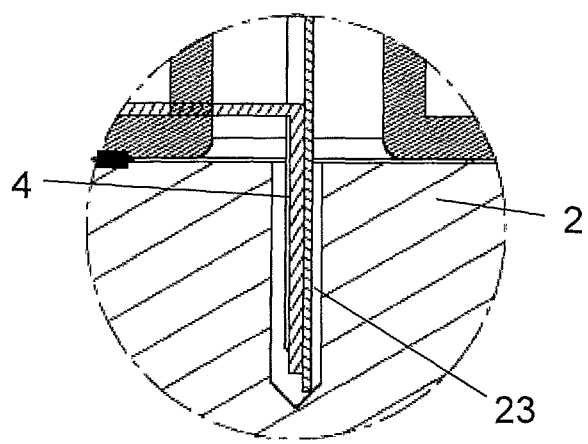
FIG. 9 is a detail view of the main part of the sensor insertion device in FIG. 8.

The guide needle 23 is detachably held by the guide needle holder 23a. The guide needle 23 goes through a through-hole 24 (see FIGS. 3A and 3B) in the biological information measuring device 3 inside the sensor insertion device 1, and projects below the biological information measuring device 3. As shown in FIGS. 7 and 8, the guide needle 23 goes in and out of the lower end opening 18 when the carrier 16 slides on the inner peripheral surface side of the main body case 15. The guide needle 23 guides the sensor 4 in the insertion direction, inserts the sensor 4 into the upper arm 2 of the patient, and leaves the sensor there (see FIG. 9).

As shown in FIGS. 5 and 6, the needle extraction sleeve 17 in this embodiment is molded from plastic in a long cylindrical shape. The needle extraction sleeve 17 is slidably mounted so as to cover the outer peripheral surface of the main body case 15. A grip portion 25 that is gripped by the user's hand is provided on the outer peripheral surface of the needle extraction sleeve 17 from the upper end to the lower end. That is, the grip portion 25 is provided along the lengthwise direction of the main body case 15.

Also, the grip portion 25 is gripped so as to be enclosed within the four fingers (excluding the thumb) and the palm of the user in using the sensor insertion device 1 to perform a needle insertion operation in which the biological information measuring device 3 (sensor 4) is attached to (inserted into) the upper arm 2 of the patient, and to perform a needle extraction operation in which the guide needle 23 is pulled out of the upper arm 2.

Furthermore, as shown in FIG. 5, the grip portion 25 is formed in a truncated cone shape, and is formed such that the cross sectional surface area (diameter) gradually decreases from the upper end side toward the lower end side. That is, the grip portion 25 is formed such that the upper end side has a larger cross sectional surface area (diameter) than the lower end side, with the lower end side gripped by the little finger having the smallest diameter.

In the state prior to the needle insertion operation shown in FIG. 6A, a needle insertion lock protrusion (first protrusion) 26 of the needle insertion button 14 is engaged in a needle insertion lock hole (engagement hole) 27 of the main body case 15 inside the sensor insertion device 1 as shown in FIG. 7. Consequently, the needle insertion button 14 is held with respect to the main body case 15 in the insertion direction.

Also, as shown in FIG. 7, a rod-shaped arm 29 that is disposed along the lengthwise direction of the needle extraction sleeve 17 is provided on the inner peripheral surface side of the needle extraction sleeve 17. The arm 29 has a lock protrusion 30 provided at its lower end so as to project radially inward.

Furthermore, the carrier 16 has two through-holes (a first lock hole 31 and second lock hole 32) formed so as to go through the long cylindrical wall surface at positions lower than the central portion in the lengthwise direction. The first lock hole 31 and the second lock hole 32 are disposed in that order starting from the lower side in the lengthwise direction of the carrier 16. That is, the second lock hole 32 is disposed adjacent to and above the first lock hole 31.

Here, in the state prior to the needle insertion operation shown in FIG. 7, the lock protrusion 30 is engaged in the lower first lock hole 31. This engagement causes the needle extraction sleeve 17 to be held by the carrier 16. Since the carrier 16 is linked to the needle insertion button 14, the needle extraction sleeve 17 is held with respect to the main body case 15.

Therefore, the needle extraction sleeve 17 cannot slide with respect to the main body case 15 prior to the needle insertion operation, so the needle extraction sleeve 17 will not slide when the user is grasping the needle extraction sleeve 17 to perform needle insertion.

As a result, the sensor insertion device 1 can be stably held against the upper arm 2.

Here, when the sensor insertion device 1 of this embodiment is used to attach the biological information measuring device 3 to the upper arm 2 of the patient, the user performs a needle insertion operation and a needle extraction operation on the sensor insertion device 1.

First, the needle insertion operation will be specifically described.

As shown in FIG. 7, the user puts the biological information measuring device 3 in the holder 22 of the sensor insertion device 1. After this, as shown in FIG. 6A, the user grasps the grip portion 25 by the four fingers (excluding the thumb) and the palm, and places the lower end of the sensor insertion device 1 against the patient's upper arm 2. At this point, the elongated main body case 15 is squeezed in the user's hand via the grip portion 25 provided along the lengthwise direction so as to cover the outer peripheral surface side of the main body case 15. That is, since the sensor insertion device 1 is being squeezed in the user's hand, the sensor insertion device 1 is stably placed against the upper arm 2.

From this state, as shown in FIG. 6B, when the user performs a needle insertion operation of pressing the needle insertion button 14 with his thumb with at least a specific amount of force, the needle insertion lock protrusion 26 of the needle insertion button 14 is disengaged from needle insertion lock hole 27 of the main body case 15 as shown in FIG. 7. Consequently, the hold of the needle insertion button 14 with respect to the main body case 15 in the insertion direction is released, and the button is pushed all the way in toward the lower end opening 18.

This pressing force is transmitted to the carrier 16 via the pressing hole 21 in which is engaged the pressing tab 20 provided at the lower end of the needle insertion button 14.

When the carrier 16 slides downward, the lock protrusion 30 of the needle extraction sleeve 17 comes out of the first lock hole 31 and is disengaged, so the carrier 16 is pushed in toward the lower end opening 18.

The carrier 16 slides toward the lower end opening 18 side in the main body case 15, and the metal guide needle 23 is pushed out from the lower end opening 18 (the lower side in FIG. 8) as shown in FIG. 8. Then, the guide needle 23 and the sensor 4 guided by the guide needle 23 are inserted into the patient's upper arm 2 (see FIG. 9). That is, the guide needle 23 guides the sensor 4 in the insertion direction and inserts the sensor 4 into the upper arm 2.

At this point, the rear surface side of the biological information measuring device 3 comes into contact with the upper arm 2, and is bonded to the upper arm 2 by the an adhesive portion 6.

In this way, the carrier 16 is operated with the needle insertion button 14, and the needle insertion operation is performed.

As shown in FIG. 8, at the lower end of the needle insertion button 14, the pressing tab 20 is pulled out of the pressing hole 21 by a releasing tab 28 of the main body case 15, and the pressing tab 20 is disengaged from the pressing hole 21. Consequently, the carrier 16 is released from the needle insertion button 14.

Also, in the carrier 16, the lock protrusion 30 of the needle extraction sleeve 17 is engaged with the second lock hole 32. This engagement creates a state in which the carrier 16 is operated by the needle extraction sleeve 17.

Since the carrier 16 is released from the needle insertion button 14, the needle extraction sleeve 17 and the carrier 16 can slide with respect to the main body case 15 (can be operated).

As a result, the user can perform a needle extraction operation using the needle extraction sleeve 17.

The above operation concludes the needle insertion operation of the sensor insertion device 1.

The needle extraction operation of the sensor insertion device 1 will now be described.

Figure 6C:
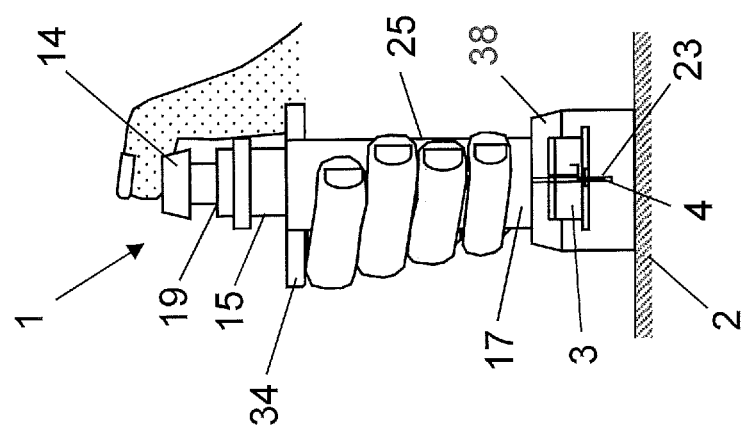
Figure 10:
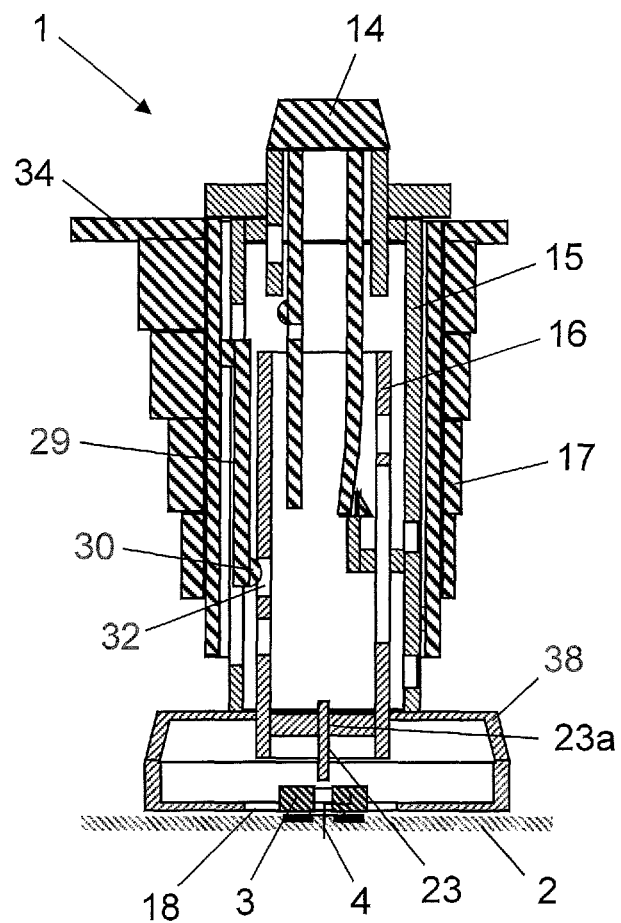
FIG. 10 is a cross section of the sensor insertion device in FIG. 6C.

The user pulls up just the needle extraction sleeve 17 toward the upper end opening 19 side as shown in FIGS. 6b and 6c while holding down the upper surface of the needle insertion button 14 with the thumb during a needle insertion operation. Then, as shown in FIG. 10, the carrier 16 linked to the needle extraction sleeve 17 is pulled up by the engagement between the lock protrusion 30 and the second lock hole 32. Therefore, the guide needle 23 fixed to the carrier 16 is also pulled up, and is pulled out of the patient's upper arm 2. As a result, just the guide needle 23 is taken out of the upper arm 2 of the patient, leaving the sensor 4 behind in the upper arm 2, and this completes the installation of the biological information measuring device 3.

In this embodiment, a configuration is employed in which the needle extraction sleeve 17 used for the needle extraction operation can also be utilized for the needle insertion operation.

More specifically, as mentioned above, the needle extraction sleeve 17 is formed in a long cylindrical shape, and the grip portion 25 is provided on the outer peripheral surface of this sleeve, from the upper end to the lower end. That is, the grip portion 25 is provided along the lengthwise direction of the main body case 15.

Therefore, as shown in FIGS. 6a and 6b, when the user presses the needle insertion button 14 with the thumb in a needle insertion operation, the grip portion 25 of the needle extraction sleeve 17 is squeezed with the user's four fingers (excluding the thumb) and palm. This squeezing of the grip portion 25 stabilizes the alignment of the sensor insertion device 1.

At this point, since the grip portion 25 is provided along the lengthwise direction of the main body case 15, the axis formed by the squeezing hand is the same as the push-down axis when pushing in the needle insertion button 14.

Therefore, the needle insertion button 14 is pressed down along the axis formed by the squeezing hand in a state in which the alignment of the sensor insertion device 1 is stable, so the sensor insertion device 1 is less likely to shake to the left and right.

As a result, the alignment of the sensor insertion device 1 is stable during the needle insertion operation, which makes the device easier to use.

Furthermore, in this embodiment, in order to stabilize the alignment of the sensor insertion device 1, the grip portion 25 of the needle extraction sleeve 17 is formed in a truncated cone shape as shown in FIG. 5, and is formed so that the diameter increases in stages from the lower end side toward the upper end side. That is, the grip portion 25 is formed so that the cross sectional surface area is larger on the upper end side than on the lower end side, and is in the form of an inverted truncated cone, with the lower end side that is gripped by the little finger being the smallest in diameter.

Therefore, the grip portion 25 can be grasped with the gripping force of the little finger and the ring finger of the patient, so the thumb can move freely.

Therefore, the user can press the needle insertion button 14 down along the axis with a freely movable thumb, so the alignment of the sensor insertion device 1 can be further stabilized during a needle insertion operation.

Furthermore, the grip portion 25 is provided along the axis of the main body case 15. Therefore, in an operation to extract the guide needle 23, the user holds down the upper surface of the needle insertion button 14 with his thumb, while pulling the squeezed needle extraction sleeve 17 up to the upper end opening 19 side from the state shown in FIG. 6B to the state shown in FIG. 6C.

That is, when it is time for the needle extraction operation, the user does not need to adjust his grip on the grip portion 25 he was squeezing in the needle insertion operation.

The grip portion 25 here is formed such that its diameter (cross sectional surface area) increases from the lower end side toward the upper end side. Therefore, the user performs the needle extraction operation by lifting (pulling up) the squeezing four fingers (excluding the thumb) toward the thumb, and this allows the alignment of the sensor insertion device 1 during the needle extraction operation to be stabilized.

Also, in this embodiment, as shown in FIG. 5, the outer surface of the grip portion 25 has three (at least one) ribs 33 protruding from the upper end to the lower end in the outer peripheral direction of the needle extraction sleeve 17.

This allows the patient to securely grasp the grip portion 25 with the four fingers to (excluding the thumb) so that the grip portion 25 does not slip in the lengthwise direction, so the needle extraction sleeve 17 can be stably operated during the needle insertion operation and the needle extraction operation.

As a result, the alignment of the sensor insertion device 1 can be stabilized during the needle extraction operation.

Furthermore, in this embodiment, the needle extraction sleeve 17 has the finger rest collar 34 provided at the upper end of the grip portion 25. The finger rest collar 34 is formed so as to protrude from a part of the outer peripheral surface of the grip portion 25 in a direction substantially perpendicular to the insertion direction of the sensor 4.

Therefore, as shown in FIG. 6B, the user places the upper side of the index finger against the finger rest collar 34 to perform the needle extraction operation, so that the force of the index finger is transmitted through the finger rest collar 34 to the needle extraction sleeve 17, and this allows the user to operate the needle extraction sleeve 17 stably.

As a result, the alignment of the sensor insertion device 1 during the needle extraction operation can be further stabilized.

Figure 11:
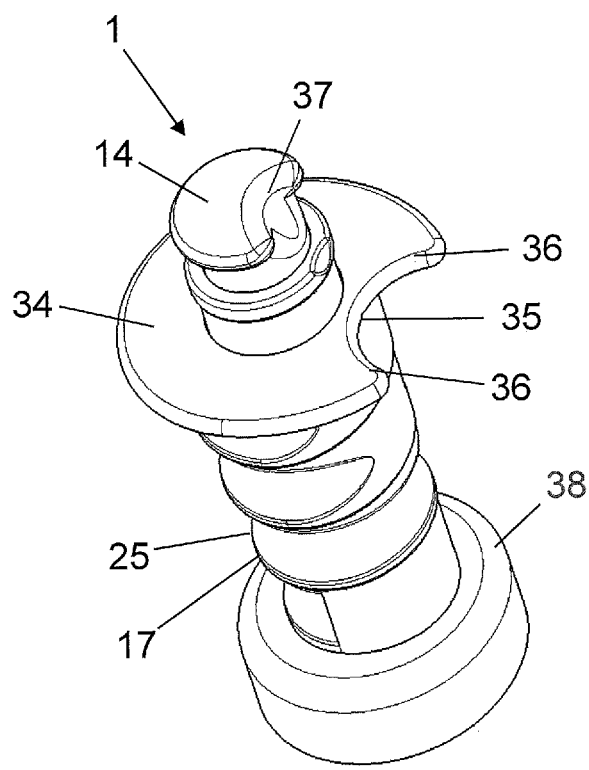
FIG. 11 is an oblique view of the sensor insertion device in FIG. 1 from above.

Also, as shown in FIG. 11, the finger rest collar 34 is provided with a cutout recess 35 formed so that part of the finger rest collar 34 is cut out from its outer periphery toward the central axis of the needle extraction sleeve 17.

The cutout recess 35 is formed such that the recess faces in a direction perpendicular to the lengthwise direction of the needle extraction sleeve 17. The cutout recess 35 guides the movement of the user's thumb, and guide portions 36 are provided on both sides thereof.

Therefore, the user's thumb is naturally guided to the central part (axial portion) of the needle insertion button 14 via the cutout recess 35. This makes it easy for the user to press the needle insertion button 14 along its axis.

As a result, the alignment of the sensor insertion device 1 during the needle insertion operation can be stabilized.

Also, a cutout 37 is formed on the same side as the cutout recess 35 at the upper end of the needle insertion button 14. As a result, the user's thumb is guided to the upper end of the needle insertion button 14 by the cutout 37.

Figure 12:
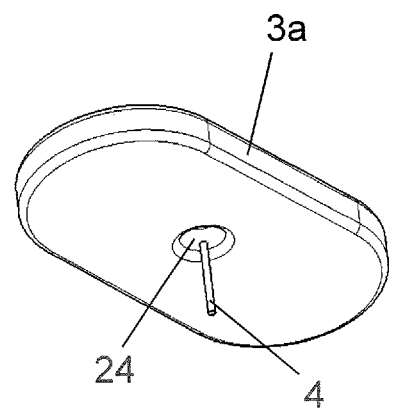
FIG. 12 is an oblique view of a biological information measuring device attached by means of the sensor insertion device according to Embodiment 1 of the present invention.
Figure 13:
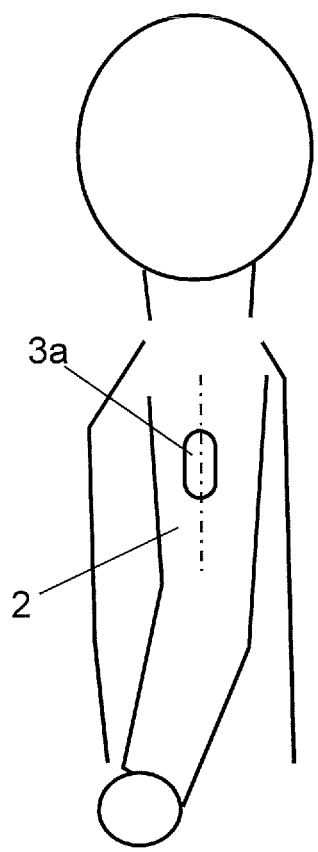
FIG. 13 is a view showing the attached state of the biological information measuring device in FIG. 12.

As shown in FIG. 12, when the external shape of a biological information measuring device 3a is elliptical, the biological information measuring device 3a is attached so that its lengthwise direction is aligned with the lengthwise direction of the upper arm 2, as shown in FIG. 13. This results in an attached state in which the orientation of the biological information measuring device 3a is stabilized.

Figure 14:
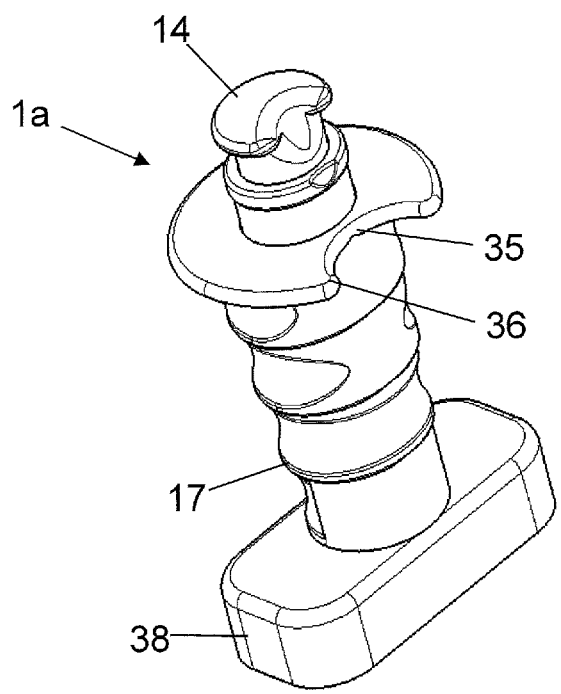
FIG. 14 is an oblique view of the sensor insertion device to which the biological information measuring device in FIG. 12 is attached.

In this embodiment, as shown in FIG. 14, in a sensor insertion device 1a, a rectangular base portion 38 may be provided at the lower end portion of the main body case 15.

In this case, the rectangular base portion 38 is disposed so that its lengthwise direction is perpendicular to the axis of the main body case 15. Furthermore, the cutout recess 35 of the needle extraction sleeve 17 is formed so that the recess faces in a direction perpendicular to the lengthwise direction of the base portion 38. The biological information measuring device 3a shown in FIG. 12 is held in the base portion 38 with its lengthwise direction aligned with the lengthwise direction of the base portion 38.

The configuration of the sensor insertion device 1a is the same as that of the sensor insertion device 1 described above except for the base portion 38.

Here, when the patient himself squeezes the needle extraction sleeve 17 of the sensor insertion device 1a with the right hand, for example, the patient's thumb is guided by the guide portion 36 of the cutout recess 35 to the needle insertion button 14, as described above. At this point, since the cutout recess 35 is formed facing in a direction perpendicular to the lengthwise direction of the base portion 38, the right hand of the patient who squeezing the needle extraction sleeve 17 is in a state of being perpendicular to the lengthwise direction of the base portion 38.

Figure 15:
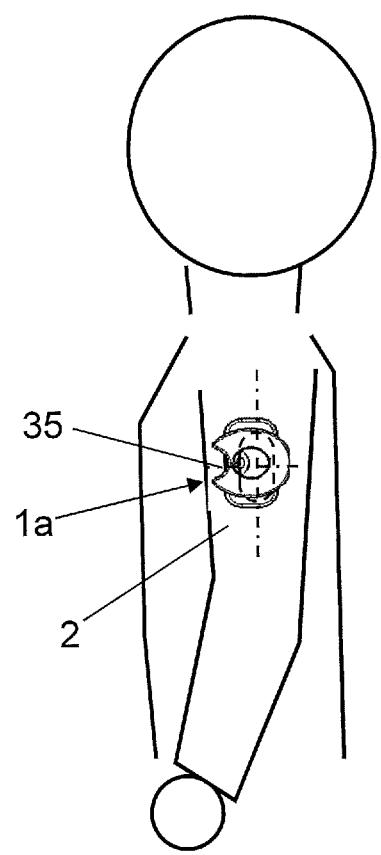
FIG. 15 is a view showing the usage state of the sensor insertion device in FIG. 14.

In this state, as shown in FIG. 15, when the patient bends his right arm and brings the base portion 38 of the sensor insertion device 1a into contact with his left upper arm 2, the lengthwise direction of the base portion 38 will coincide with the lengthwise direction of the upper arm 2. That is, the lengthwise direction of the biological information measuring device 3a coincides with the lengthwise direction of the patient's upper arm 2.

After this, as discussed above, when the patient himself performs a needle insertion operation and a needle extraction operation, the biological information measuring device 3a is attached with its lengthwise direction substantially coinciding with the lengthwise direction of the left arm of the patient, as shown in FIG. 12.

As a result, the biological information measuring device 3a can be attached in a stable state.

INDUSTRIAL APPLICABILITY

The present invention is expected to find use as a sensor insertion device that inserts a sensor for measuring biological information into a patient's body in order to perform continuous blood glucose measurement, for example.

REFERENCE SIGNS LIST 1, 1a sensor insertion device
2 upper arm
3, 3a biological information measuring device
4 sensor
5 subcutaneous tissue
6 adhesive portion
7 measurement unit
8 controller
9 battery
10 temperature sensor
11 memory unit
12 communication unit
13 mobile phone
14 needle insertion button
15 main body case
16 carrier
17 needle extraction sleeve
18 lower end opening
to 19 upper end opening
20 pressing tab
21 pressing hole
22 holder
23 guide needle
23a guide needle holder
24 through-hole
25 grip portion
26 needle insertion lock protrusion (first protrusion)
27 needle insertion lock hole (engagement hole)
28 releasing tab
29 arm
30 lock protrusion
31 first lock hole
32 second lock hole
33 rib
34 finger rest collar
35 cutout recess
36 guide portion
37 cutout
38 base portion

The invention claimed is:

1. A sensor insertion device for inserting a sensor for measuring biological information into a body of a patient, the sensor insertion device comprising:
   a cylindrical main body case having a lower end opening and an upper end opening;
   a needle insertion button that is disposed slidably in and out of the upper end opening on an inside of the cylindrical main body case, and configured to be operated by a user when performing needle insertion;
   a carrier that is provided in the cylindrical main body case and linked to the needle insertion button;
   a guide needle holder that is provided at a lower end portion of the carrier and configured to detachably hold a guide needle that is configured to be inserted into the body of the patient when guiding the sensor in an insertion direction;
   a cylindrical needle extraction sleeve that is provided slidably around an outer periphery of the cylindrical main body case; and
   a grip portion that is provided along a lengthwise direction of the cylindrical main body case on an outer peripheral surface side of the cylindrical needle extraction sleeve, and configured to be gripped by a hand of the user when inserting the sensor;
   wherein:
   the grip portion has a finger rest collar that is provided at an upper end portion of the grip portion, and protrudes in a direction intersecting the insertion direction;
   the finger rest collar has a cutout recess for guiding a finger of the user; and
   a cutout is defined at an upper end of the needle insertion button on a same side as the cutout recess of the finger rest collar.

2. The sensor insertion device according to claim 1, wherein a needle insertion operation is configured to be carried out by operating the needle insertion button with a thumb of the user in a state in which the grip portion is being gripped.

3. The sensor insertion device according to claim 2, wherein, after the needle insertion operation, a needle extraction operation is configured to be carried out by operating the cylindrical needle extraction sleeve such that the hand of the user gripping the grip portion is pulled upward while the thumb of the user is still pressing the needle insertion button.

4. The sensor insertion device according to claim 1, wherein:
the needle insertion button has a cylindrical shape and a protrusion that protrudes from an outer peripheral surface of the cylindrical shape of the needle insertion button;
the cylindrical main body case has a cylindrical shape and an engagement hole that extends through a part of the cylindrical shape of the cylindrical main body case such that the protrusion is configured to engage with the engagement hole; and
the needle insertion button is configured to be held with respect to the cylindrical main body case by engagement between the protrusion and the engagement hole until a needle insertion operation is performed with the needle insertion button.

5. The sensor insertion device according to claim 1, wherein an upper end side of the grip portion has a larger cross sectional surface area than a lower end side of the grip portion.

6. The sensor insertion device according to claim 5, wherein the grip portion has a truncated cone shape.

7. The sensor insertion device according to claim 1, wherein the grip portion has one or more ribs protruding from an outer peripheral surface of the cylindrical needle extraction sleeve, from an upper end to a lower end.

8. The sensor insertion device according to claim 1, wherein the cylindrical main body case has a base portion that is provided at a lower end portion of the cylindrical main body case, and configured to come into contact with a skin of the patient.

9. The sensor insertion device according to claim 8, wherein the base portion has an elongated shape.

10. The sensor insertion device according to claim 9 wherein:
a lengthwise direction of the elongated shape is perpendicular to the lengthwise direction of the cylindrical main body case; and
the cutout recess of the finger rest collar is defined with a recessed portion facing in a direction which is perpendicular to a lengthwise direction of the base portion.

* * * * *